US011424831B2

(12) United States Patent
Kwon

(10) Patent No.: US 11,424,831 B2
(45) Date of Patent: Aug. 23, 2022

(54) FREQUENCY SWEPT SOURCE APPARATUS

(71) Applicant: ELECTRONICS AND TELECOMMUNICATIONS RESEARCH INSTITUTE, Daejeon (KR)

(72) Inventor: Oh Kee Kwon, Sejong-si (KR)

(73) Assignee: Electronics and Telecommunications Research Institute, Daejeon (KR)

( * ) Notice: Subject to any disclaimer, the term of this patent is extended or adjusted under 35 U.S.C. 154(b) by 0 days.

(21) Appl. No.: 17/539,042

(22) Filed: Nov. 30, 2021

(65) Prior Publication Data

US 2022/0173812 A1 Jun. 2, 2022

(30) Foreign Application Priority Data

Dec. 1, 2020 (KR) .................. 10-2020-0165279

(51) Int. Cl.
*H04B 10/50* (2013.01)
*H04L 7/00* (2006.01)
*H04B 10/079* (2013.01)

(52) U.S. Cl.
CPC ....... *H04B 10/504* (2013.01); *H04B 10/0793* (2013.01); *H04L 7/0041* (2013.01)

(58) Field of Classification Search
CPC .. H04B 10/504; H04B 10/0793; H04L 7/0041
USPC ....................................................... 398/115
See application file for complete search history.

(56) References Cited

U.S. PATENT DOCUMENTS

| 7,003,180 B2* | 2/2006 | Richardson ........... G02F 1/3515 |
| | | 385/27 |
| 9,348,195 B2* | 5/2016 | Kwon ..................... G02F 1/383 |
| 2002/0044723 A1* | 4/2002 | Hironishi ................ H04J 14/02 |
| | | 385/24 |
| 2004/0017833 A1 | 1/2004 | Cundiff et al. |
| 2004/0208414 A1* | 10/2004 | Lee ......................... H04J 14/08 |
| | | 385/24 |
| 2006/0187537 A1 | 8/2006 | Huber et al. |

(Continued)

OTHER PUBLICATIONS

Ioan L. Gheorma et al., "Flat Frequency Comb Generation With an Integrated Dual-Parallel Modulator", IEEE Photonics Technology Letters, vol. 19, No. 13, Jul. 1, 2007.

(Continued)

*Primary Examiner* — Abbas H Alagheband
(74) *Attorney, Agent, or Firm* — Rabin & Berdo, P.C.

(57) ABSTRACT

Disclosed is a frequency swept source apparatus including a mode locking laser that outputs an input optical signal having first to n-th frequency components, a transmission delay controller that generates first to m-th sub-optical signals, each of which includes at least one component of the first to n-th frequency components, and outputs a delay optical signal obtained by sequentially delaying the first to m-th sub-optical signals. The transmission delay controller includes a demultiplexer that outputs the first to m-th sub-optical signals to first to m-th channels based on the input optical signal, respectively, a path delay unit that adjusts lengths of optical paths of the first to m-th channels so as to be different from one another, a refractive index controller that adjusts a refractive index of each of the first to m-th channels, and a multiplexer that combines the first to m-th sub-optical signals.

14 Claims, 11 Drawing Sheets

(56) References Cited

U.S. PATENT DOCUMENTS

2011/0135309 A1* 6/2011 Lee .................. H04B 10/506
  398/79
2015/0002918 A1* 1/2015 Kwon .................. H01S 5/0687
  359/239

OTHER PUBLICATIONS

R. P. Scott et al., "3.5-THz Wide, 175 Mode Optical Comb Source", OFC/NFOEC 2007—2007 Conference on Optical Fiber Communication and the National Fiberoptic Engineers Conference, Mar. 25-29, 2007.

* cited by examiner

FREQUENCY SWEPT SOURCE APPARATUS

CROSS-REFERENCE TO RELATED APPLICATIONS

This application claims priority under 35 U.S.C. § 119 to Korean Patent Application No. 10-2020-0165279 filed on Dec. 1, 2020, in the Korean Intellectual Property Office, the disclosures of which are incorporated by reference herein in their entireties.

BACKGROUND

Embodiments of the present disclosure described herein relate to a light source apparatus, and more particularly, relate to a frequency swept source apparatus that delays an optical signal depending on a frequency component.

A frequency swept source (FSS) is used as a core light source in bio or medical 3D optical coherent tomography (OCT), automatic optical inspection (AOI) for monitoring and diagnosing an industrial process, spectroscopy for analyzing a semiconductor and polymer material, an environmental gas monitoring device, optical communication system equipment, or the like.

Nowadays, to implement a real-time high-quality measurement image, a swept source-OCT (SS-OCT) needs a light source having a high swept repetition rate. The swept repetition rate of several megahertz (MHz) is required to obtain an image rate having a short period (e.g., 0.2 seconds or less) for a three-dimensional measurement image (e.g., a full 3D image of 500×500×500 pixels).

In the past, advantages and disadvantages are distinguished in terms of price, volume, and performance for each implementation form, and thus the form has been limited for each application field. However, while functional configurations have been recently subdivided or merged, related technologies have been developed and performance has been improved. Accordingly, disadvantages for each type are continuously improved and the fields of application are being overlapped.

SUMMARY

Embodiments of the present disclosure provide a frequency swept source apparatus that delays an optical signal depending on a frequency component.

According to an embodiment, a frequency swept source apparatus includes a mode locking laser that outputs an input optical signal having first to n-th frequency components, a transmission delay controller that generates first to m-th sub-optical signals, each of which includes at least one component of the first to n-th frequency components, based on the input optical signal and outputs a delay optical signal obtained by sequentially delaying the first to m-th sub-optical signals. The transmission delay controller includes a demultiplexer that outputs the first to m-th sub-optical signals to first to m-th channels based on the input optical signal, respectively, a path delay unit that adjusts lengths of optical paths of the first to m-th channels so as to be different from one another, a refractive index controller that adjusts a refractive index of each of the first to m-th channels, and a multiplexer that combines the first to m-th sub-optical signals passing through the first to m-th channels and outputs the delay optical signal. The 'n' is a natural number. The 'm' is a natural number less than the 'n'.

In embodiment, the demultiplexer is further configured to output the first sub-optical signal including a lowest frequency component among the first to n-th frequency components and to output the m-th sub-optical signal including a highest frequency component among the first to n-th frequency components.

In an embodiment, the path delay unit is further configured to adjust the lengths of the optical paths of the first to m-th channels so as to be increased sequentially.

In an embodiment, the path delay unit is further configured to adjust the lengths of the optical paths of the first to m-th channels so as to be decreased sequentially.

In an embodiment, the refractive index controller is further configured to increase the refractive index of each of the first to m-th channels in proportion to an external voltage.

In an embodiment, the transmission delay controller is further configured to determine a time interval between a first time point, at which the first sub-optical signal is output, and a second time point at which the m-th sub-optical signal is output, based on a length difference between the optical path of the first channel and the optical path of the m-th channel.

In an embodiment, the transmission delay controller is further configured to determine a time interval between a first time point, at which the first sub-optical signal is output, and a second time point at which the m-th sub-optical signal is output, based on the refractive index of each of the refractive index controller.

In an embodiment, the 'n' is an integer multiple of the 'm'.

In an embodiment, the frequency swept source apparatus further includes a pulse compressor that compresses a pulse of the input optical signal from the mode locking laser and outputs a compression optical signal, a band pass filter that blocks a noise component of the compression optical signal and outputs a band pass signal to the transmission delay controller, and an amplifier that amplifies the delay optical signal from the transmission delay controller.

According to an embodiment, a frequency swept source apparatus includes a mode locking laser that outputs an input optical signal having first to n-th frequency components, a reflective delay controller that generates first to m-th sub-optical signals, each of which includes at least one component of the first to n-th frequency components, based on the input optical signal and outputs a delay optical signal obtained by sequentially delaying the first to m-th sub-optical signals, and a circulator that provides a first path from the mode locking laser to the reflective delay controller and a second path from the reflective delay controller to a light emitting unit. The reflective delay controller includes a channel separator that outputs the first to m-th sub-optical signals to first to m-th channels based on the input optical signal, respectively, and to output the delay optical signal, which is obtained by combining first to m-th reflective sub-optical signals from the first to m-th channels, to the circulator, a path delay unit that adjusts lengths of optical paths of the first to m-th channels so as to be different from one another, a refractive index controller that adjusts a refractive index of each of the first to m-th channels, and a reflector that reflects the first to m-th sub-optical signals from the first to m-th channels and to output the first to m-th reflective sub-optical signals to the first to m-th channels. The 'n' is a natural number. The 'm' is a natural number less than the 'n'.

In an embodiment, the channel separator is further configured to output the first sub-optical signal including a lowest frequency component among the first to n-th frequency components to the first channel based on the input optical signal and to output the m-th sub-optical signal including a highest frequency component among the first to n-th frequency components to the m-th channel based on the input optical signal.

In an embodiment, the path delay unit is further configured to adjust the lengths of the optical paths of the first to m-th channels so as to be increased sequentially.

In an embodiment, the path delay unit is further configured to adjust the lengths of the optical paths of the first to m-th channels so as to be decreased sequentially.

In an embodiment, the frequency swept source apparatus further includes a pulse compressor that receives the input optical signal from the mode locking laser through the first path, compresses a pulse of the input optical signal, and outputs a compression optical signal, a band pass filter that blocks a noise component of the compression optical signal and outputs a band pass signal to the circulator through the first path, and an amplifier that receives the delay optical signal from the circulator through the second path, amplifies the delay optical signal, and outputs an amplification optical signal to the light emitting unit through the second path.

BRIEF DESCRIPTION OF THE FIGURES

The above and other objects and features of the present disclosure will become apparent by describing in detail embodiments thereof with reference to the accompanying drawings.

DETAILED DESCRIPTION

Below, embodiments of the present disclosure will be described in detail and clearly to such an extent that an ordinary one in the art easily implements the present disclosure.

Figure 1:
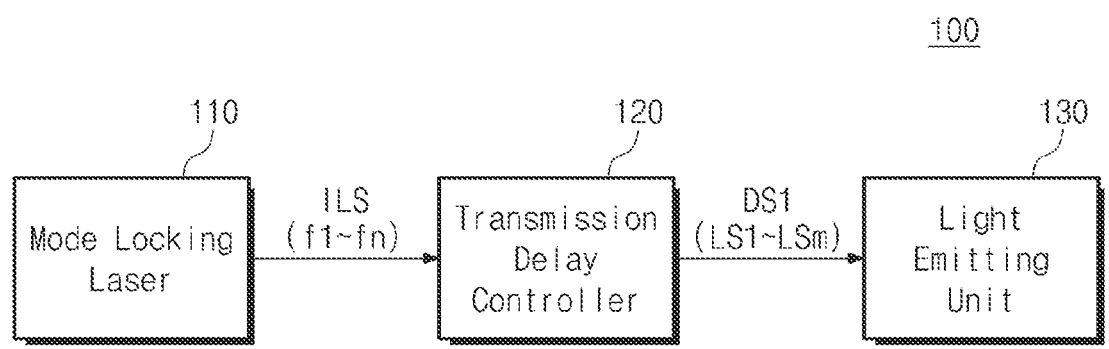
FIG. 1 is a block diagram illustrating a frequency swept source apparatus, according to an embodiment of the present disclosure.

FIG. 1 is a block diagram illustrating a frequency swept source apparatus, according to an embodiment of the present disclosure. Referring to FIG. 1, a frequency swept source apparatus 100 is illustrated. The frequency swept source apparatus 100 may be an apparatus for sequentially outputting an optical signal by delaying a time to arrive at an output terminal for each frequency.

For example, the frequency swept source apparatus 100 may be used as a core light source in bio or medical 3D optical coherent tomography (OCT), automatic optical inspection (AOI) for monitoring and diagnosing an industrial process, spectroscopy for analyzing a semiconductor and polymer material, an environmental gas monitoring device, optical communication system equipment, or the like.

The frequency swept source apparatus 100 may include a mode locking laser 110, a transmission delay controller 120, and a light emitting unit 130.

The mode locking laser 110 may output an input optical signal ILS having a plurality of frequency components. For example, the input optical signal ILS may include first to n-th frequency components f1 to fn. The first to n-th frequency components f1 to fn may be optical signals respectively corresponding to sequentially increasing frequencies. 'n' may indicate the number of frequency components included in the input optical signal ILS. 'n' may be an arbitrary natural number.

The input optical signal ILS generated by the mode locking laser 110 may have a pulse width having a short time interval. For example, the pulse width of the input optical signal ILS may have a time interval of several femto seconds (fs) or several pico seconds (ps).

The transmission delay controller 120 may generate first to m-th sub-optical signals LS1 to LSm having a plurality of frequency components based on the input optical signal ILS, and then may output a delay optical signal DS1. The delay optical signal DS1 may be a signal obtained by combining the first to m-th sub-optical signals LS1 to LSm, which are sequentially delayed. Input and output terminals of the transmission delay controller 120 are located in opposite directions to each other, and thus the transmission delay controller 120 is referred to as a transmission delay controller.

Each of the first to m-th sub-optical signals LS1 to LSm may include at least one component among the first to n-th frequency components. For example, the first sub-optical signal LS1 may include the lowest frequency component among the first to n-th frequency components f1 to fn. The m-th sub-optical signal LSm may include the highest frequency component among the first to n-th frequency components f1 to fn. 'm' may indicate the number of channels of the transmission delay controller 120. The channels of the transmission delay controller 120 will be described in detail with reference to FIG. 2. That is, 'n' may be an arbitrary natural number. 'm' may be any natural number less than 'n'. However, the scope of the present disclosure is not limited thereto.

More specifically, for example, when 'n' is 3000 and 'm' is 100, the first sub-optical signal LS1 may include first to thirtieth frequency components f1 to f30. The second sub-optical signal LS2 may include 31st to 60th frequency components f31 to f60. The m-th sub-optical signal LSm (i.e., a 100th sub-optical signal LS100) may include 2971st to 3000th frequency components f2971 to f3000. However, the scope of the present disclosure is not limited thereto. 'n' and 'm' may increase or decrease, and the number of frequency components included in each sub-optical signal may increase or decrease.

The light emitting unit 130 may receive the delay optical signal DS1 from the transmission delay controller 120. The light emitting unit 130 may output the delay optical signal DS1 to the outside of the frequency swept source apparatus 100. That is, the light emitting unit 130 may be an output terminal of the frequency swept source apparatus 100.

Figure 2:
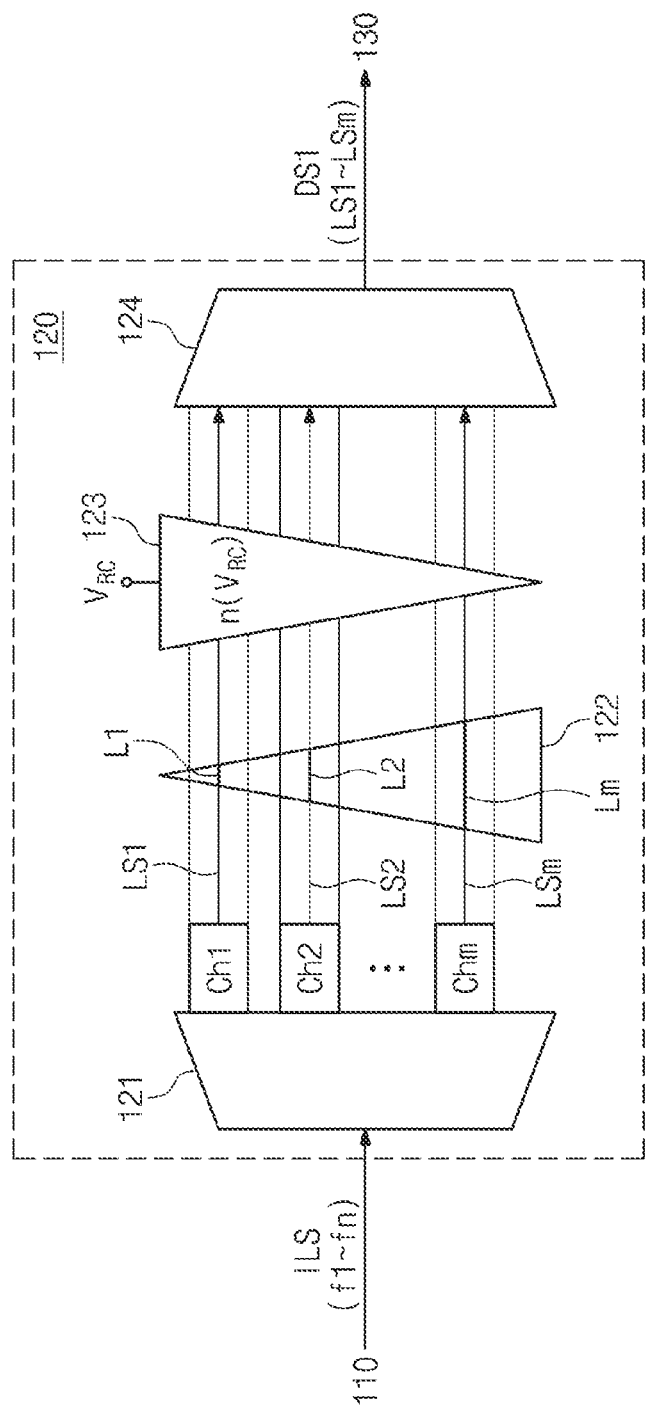
FIG. 2 is a detailed diagram of the transmission delay controller of FIG. 1.

FIG. 2 is a detailed diagram of the transmission delay controller of FIG. 1. Referring to FIG. 2, the transmission delay controller 120 is illustrated. The transmission delay controller 120 may generate the sub-optical signals LS1 to LSm based on the input optical signal ILS, and then may output the delay optical signal DS1 thus sequentially delayed. The transmission delay controller 120 may include a demultiplexer 121, a path delay unit 122, a refractive index controller 123, and a multiplexer 124.

According to an embodiment of the present disclosure, the transmission delay controller 120 adjusts optical path lengths L1 to Lm for each of channels Ch1 to Chm and adjusts a refractive index of each of the first to m-th channels Ch1 to Chm. A direct physical change is not applied to the optical signal, and thus the present disclosure has mechanical stability and high reliability.

The demultiplexer 121 may separate the input optical signal ILS based on the frequency components f1 to fn of the input optical signal ILS and may output the first to m-th sub-optical signals LS1 to LSm to the corresponding first to m-th channels Ch1 to Chm. The first to m-th channels Ch1 to Chm may be paths through which optical signals are transmitted. The first to m-th channels Ch1 to Chm may be physically or spatially separated from each other.

For example, the demultiplexer 121 may output the first sub-optical signal LS1 to the first channel Ch1. The first sub-optical signal LS1 may include a lowest frequency component among the plurality of frequency components f1 to fn of the input optical signal ILS. For example, the demultiplexer 121 may output the m-th sub-optical signal LSm to the m-th channel Chm. The m-th sub-optical signal LSm may include a highest frequency component among the plurality of frequency components f1 to fn of the input optical signal ILS.

In an embodiment, 'n' may be an integer multiple of 'm'. When 'n' is the integer multiple of 'm', each of the sub-optical signal LS1 to LSm may include the same number of frequency components (i.e., n/m) as one another.

The path delay unit 122 and the refractive index controller 123 may receive the first to m-th sub-optical signal LS1 to LSm from the demultiplexer 121 through the first to m-th channel Ch1 to Chm. The path delay unit 122 may adjust the lengths L1 to Lm of optical paths of the first to m-th channels Ch1 to Chm so as to be different from one another.

In an embodiment, the path delay unit 122 may adjust the lengths L1 to Lm of the optical paths of the first to m-th channels Ch1 to Chm so as to be increased sequentially. For example, the length L2 of the second optical path may be longer than the length L1 of the first optical path. The length Lm of the m-th optical path may be longer than the length L2 of the second optical path. Accordingly, the time required for the first sub-optical signal LS1 to pass through the first channel Ch1 may be shorter than the time required for the second sub-optical signal LS2 to pass through the second channel Ch2. The time required for the second sub-optical signal LS2 to pass through the second channel Ch2 may be shorter than the time required for the m-th sub-optical signal LSm to pass through the m-th channel Chm.

In another embodiment, the path delay unit 122 may adjust the lengths L1 to Lm of the optical paths of the first to m-th channels Ch1 to Chm so as to be decreased sequentially. For example, the length L2 of the second optical path may be shorter than the length L1 of the first optical path. The length Lm of the m-th optical path may be shorter than the length L2 of the second optical path. Accordingly, the time required for the first sub-optical signal LS1 to pass through the first channel Ch1 may be longer than the time required for the second sub-optical signal LS2 to pass through the second channel Ch2. The time required for the second sub-optical signal LS2 to pass through the second channel Ch2 may be longer than the time required for the m-th sub-optical signal LSm to pass through the m-th channel Chm.

In an embodiment, the path delay unit 122 may be implemented in a shape such as a prism.

The refractive index controller 123 may adjust the refractive indexes ($n(V_{RC})$) of the first to m-th channels Ch1 to Chm. In an embodiment, the refractive index controller 123 may adjust the refractive indexes ($n(V_{RC})$) of the first to m-th channels Ch1 to Chm to be increased in proportion to the external voltage ($V_{RC}$).

In an embodiment, when the refractive index controller 123 increases the refractive indexes ($n(V_{RC})$) of the first to m-th channels Ch1 to Chm, the difference between the degree of refraction of the optical path of the first channel Ch1 and the degree of refraction of the optical path of the m-th channel may increase.

The refractive index controller 123 may output the first to m-th sub-optical signals LS1 to LSm to the first to m-th channels Ch1 to Chm, respectively.

In an embodiment, the refractive index controller 123 may be implemented in a shape such as a prism. For example, the refractive index controller 123 may be made of a low-loss material such as liquid crystal (LC) having a large refractive index change according to an external voltage $V_{RC}$, liquid crystal on silicon (LCoS), polymer, lead lanthanum zirconate titanate (PLZT), Pb(Mg⅓Nb⅔)O3-PbTiO3 (PMN-PT) material, or the like.

In an embodiment, the refractive index controller 123 may adjust the refractive indexes of the first to m-th channels Ch1 to Chm by using the effect of a micro heater or a carrier-induced refractive index change.

The multiplexer 124 may receive the first to m-th sub-optical signals LS1 to LSm passing through the first to m-th channels Ch1 to Chm. The multiplexer 124 may output the delay optical signal DS1 by combining the first to m-th sub-optical signals LS1 to LSm. The delay optical signal DS1 may be a signal obtained by combining the first to m-th sub-optical signals LS1 to LSm, which are sequentially delayed. The sub-optical signals LS1 to LSm may be signals that are sequentially delayed based on adjustment of the lengths of the optical paths of the channels by the path delay unit 122 and adjustment of the refractive indexes of the channels by the refractive index controller 123.

In an embodiment, the delay optical signal DS1 may be output to the light emitting unit 130 by combining the first to m-th sub-optical signals LS1 to LSm passing through the first to m-th channels Ch1 to Chm.

The delay optical signal DS1 output from the multiplexer 124 may have a delay time. The delay time may indicate a maximum deviation of sub-optical signals LS1 to LSm within one period of the delay optical signal DS1. For example, the delay time may be a time interval between a point in time when the sub-optical signal LS1 corresponding to the slowest frequency component (e.g., f1) is output within an arbitrary period and a point in time when the sub-optical signal LSm corresponding to the fastest frequency component (e.g., fn) is output within an arbitrary period.

As shown in FIG. 2, as a difference ΔT between the length L1 of the first optical path and the length Lm of the m-th optical path increases, the delay time may increase.

Furthermore, as the difference between the degree of refraction of the optical path L1 of the first channel and the degree of refraction of the optical path Lm of the m-th channel increases in the refractive index controller 123, the delay time may increase.

The delay time ΔT of the transmission delay controller 120 is described with reference to Equation 1 below.

$$\Delta T = \frac{\Delta L}{\frac{c}{n(V_{RC})}} \quad \text{[Equation 1]}$$

Equation 1 is an equation indicating a delay time. ΔT denotes a delay time. ΔL denotes a difference between the length L1 of the optical path of the first channel Ch1 and the length Lm of the optical path of the m-th channel Chm. 'c' is the speed of light. $n(V_{RC})$ is a refractive index of each of the first to m-th channels Ch1 to Chm, and is the function of $V_{RC}$. $V_{RC}$ is an external voltage.

For example, when the refractive index ($n(V_{RC})$) of each of the first to m-th channels Ch1 to Chm is 1.5 and the difference ΔL between the length L1 of the first optical path and the length Lm of the m-th optical path is 50 mm, the delay time ΔT may be 250 ps.

That is, Equation 1 may indicate that the delay time ΔT increases as the difference between the degree of refraction of the optical path L1 of the first channel and the degree of refraction of the optical path Lm of the m-th channel increases. Moreover, Equation 1 may indicates that the delay time ΔT increases as the difference ΔL between the length L1 of the optical path of the first channel Ch1 and the length Lm of the optical path of the m-th channel Chm increases.

In an embodiment, the demultiplexer 121 and the multiplexer 124 may be implemented in a bulk type, such as a bulk grating or a configuration in which a HR coating film and a thin-film narrowband filter are attached to a glass substrate.

In an embodiment, the demultiplexer 121 and the multiplexer 124 may be implemented in a waveguide type such as an arrayed waveguide grating (AWG) or a concave grating.

In an embodiment, the demultiplexer 121 and the multiplexer 124 may be implemented in an optical fiber filter type.

Figure 3:
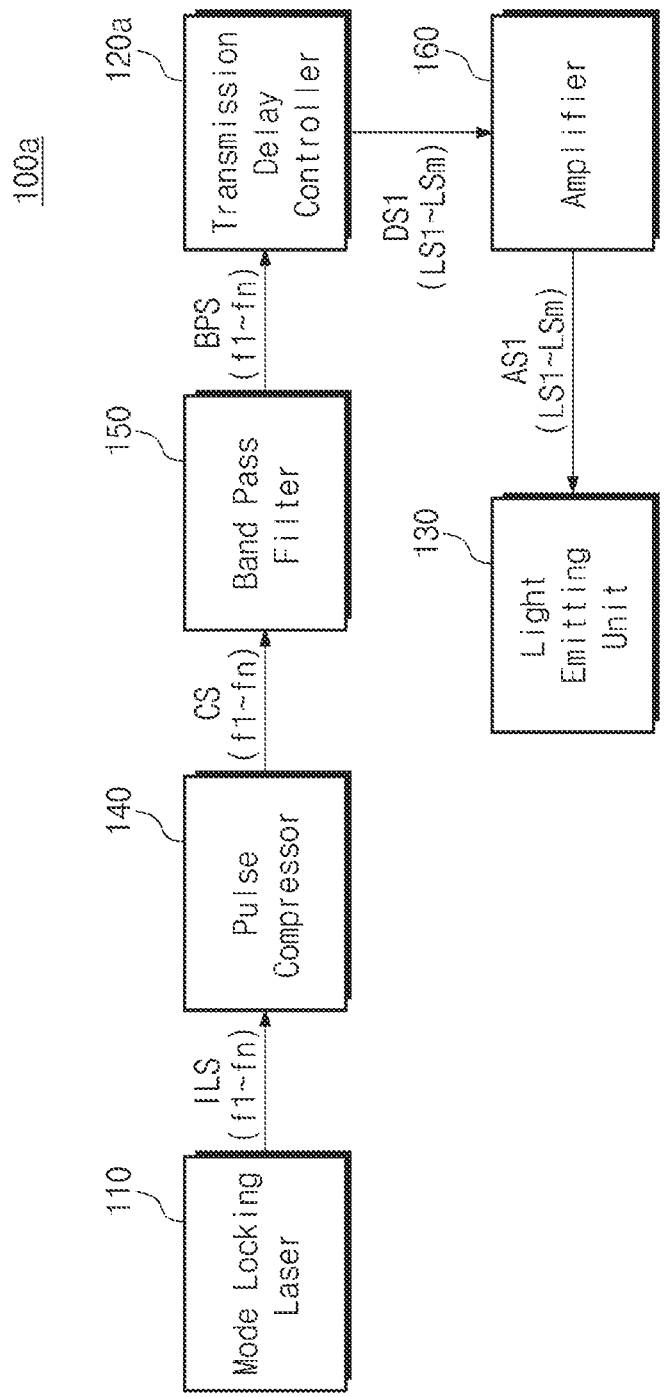
FIG. 3 is a detailed block diagram of the frequency swept source apparatus of FIG. 1.

FIG. 3 is a detailed block diagram of the frequency swept source apparatus of FIG. 1. Referring to FIG. 3, the frequency swept source apparatus 100 may include the mode locking laser 110, a transmission delay controller 120a, the light emitting unit 130, a pulse compressor 140, a band pass filter 150, and an amplifier 160. The mode locking laser 110 and the light emitting unit 130 are similar to the mode locking laser 110 and the light emitting unit 130 of FIG. 1, and thus, additional description will be omitted to avoid redundancy.

The pulse compressor 140 may receive the input optical signal ILS from the mode locking laser 110. The pulse compressor 140 may compress a pulse width of the input optical signal ILS. The pulse compressor 140 may output a compression optical signal CS to the band pass filter 150. In an embodiment, the pulse compressor 140 may expand the bandwidth of the envelope of the input optical signal ILS by compressing the pulse width of the input optical signal ILS. A detailed description of the envelope of the input optical signal ILS will be described later with reference to FIG. 7B.

The band pass filter 150 may receive the compression optical signal CS from the pulse compressor 140. The band pass filter 150 may block a noise component of the compression optical signal CS. The band pass filter 150 may output a band pass signal BPS to the transmission delay controller 120a. That is, the band pass filter 150 may function as a filter that blocks components other than components in a pass band of an optical signal. In an embodiment, the pass band of the band pass filter 150 may correspond to the first to n-th frequency components f1 to fn.

Similarly to the transmission delay controller 120 of FIGS. 1 and 2, the transmission delay controller 120a may generate the sub-optical signals LS1 to LSm and then may output the delay optical signal DS1 thus sequentially delayed. However, the input/output of the transmission delay controller 120a is different from the input/output of the transmission delay controller 120 of FIGS. 1 and 2. For example, the transmission delay controller 120a may receive the band pass signal BPS from the band pass filter 150 and may output the delay optical signal DS1 to the amplifier 160.

The amplifier 160 may receive the delay optical signal DS1 from the transmission delay controller 120a. The amplifier 160 may amplify the delay optical signal DS1. The amplifier 160 may output an amplified optical signal AS1 to the light emitting unit 130. That is, the amplifier 160 may be a module or device that amplifies an optical signal. In an embodiment, the amplifier 160 may be a gain equalizer (GE) that equally amplifies a gain of the received delay optical signal DS1.

Figure 4:
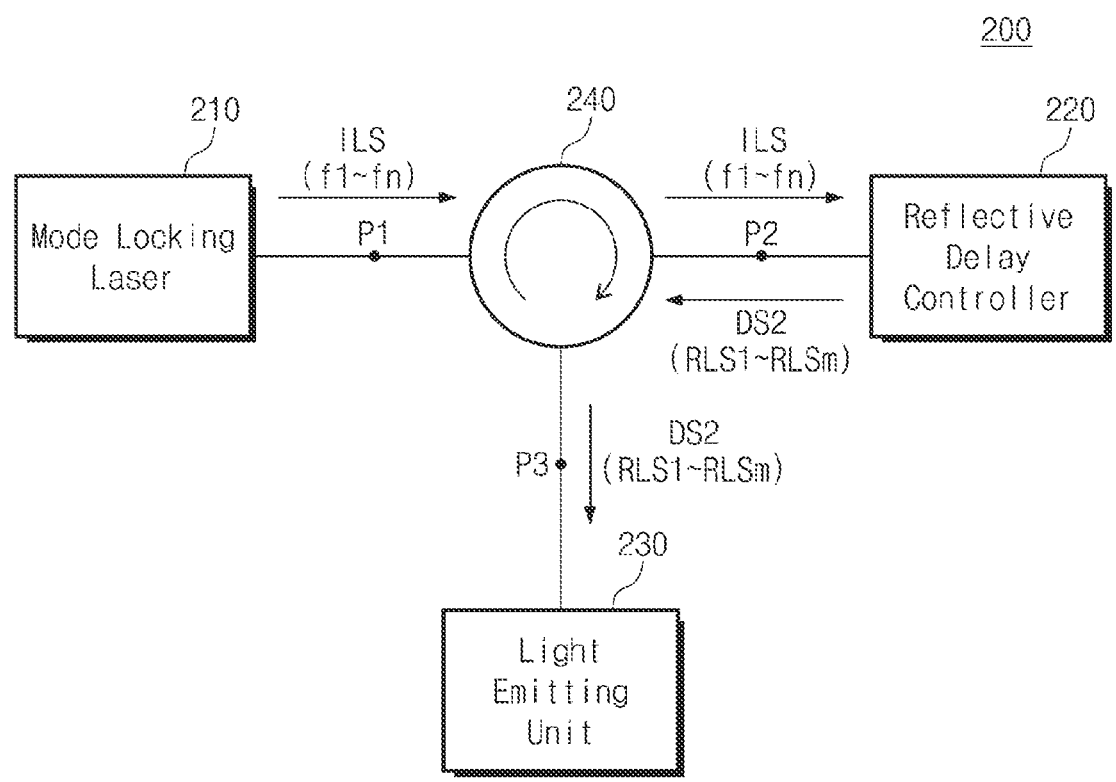
FIG. 4 is a block diagram illustrating a frequency swept source apparatus, according to another embodiment of the present disclosure.

FIG. 4 is a block diagram illustrating a frequency swept source apparatus 200, according to another embodiment of the present disclosure. Referring to FIG. 4, a frequency swept source apparatus 200 is illustrated. The frequency swept source apparatus 200 may be an apparatus that delays a time to arrive at an output terminal for each frequency and then sequentially outputs an optical signal. The frequency swept source apparatus 200 may include a mode locking laser 210, a reflective delay controller 220, a light emitting unit 230, and a circulator 240.

Similarly to the mode locking laser 110 of FIG. 1, the mode locking laser 210 may output the input optical signal ILS having a plurality of frequency components f1 to fn. The mode locking laser 210 may output the input optical signal ILS to a first port P1.

The reflective delay controller 220 may generate first to m-th reflective sub-optical signals RLS1 to RLSm having a plurality of frequency components f1 to fn based on the input optical signal ILS. The reflective delay controller 220 may output a delay optical signal DS2 to a second port P2. The delay optical signal DS2 may be signals obtained by combining first to m-th reflective sub-optical signals RLS1 to RLSm thus sequentially delayed. The reflective delay controller 220 has a reflector therein, and input and output terminals of the reflective delay controller 220 are positioned in the same direction, and thus the reflective delay controller 220 is referred to as a "reflective delay controller".

Similarly to the transmission delay controller 120 of FIG. 1, the reflective delay controller 220 may delay sub-optical signals differently for each channel. However, the reflective delay controller 220 may include a reflector (not shown) at one end of an internal channel. As sub-optical signals bidirectionally pass through channels, the delay effect of an optical path length may be doubled compared to the transmission delay controller 120 of FIG. 1. Accordingly, as compared to the transmission delay controller 120, the reflective delay controller 220 may be miniaturized and may be driven with low power.

The light emitting unit 230 may receive the delay optical signal DS2 from the circulator 240. Similarly to the light emitting unit 130 of FIG. 1, the light emitting unit 230 may output the delay optical signal DS2 to the outside of the frequency swept source apparatus 200. However, unlike the light emitting unit 130 of FIG. 1, the light emitting unit 230 may receive the delay optical signal DS1 from the third port P3.

The circulator 240 may be connected to other components 210, 220, and 230 through the first to third ports P1 to P3. For example, the circulator 240 may be connected to the mode locking laser 210 through the first port P1. The circulator 240 may be connected to the reflective delay controller 220 through the second port P2. The circulator 240 may be connected to the light emitting unit 230 through the third port P3.

In an embodiment, the circulator 240 may receive the input optical signal ILS through the first port P1. The circulator 240 may output the input optical signal ILS to the reflective delay controller 220 through the second port P2. Also, the circulator 240 may receive the delay optical signal DS2 from the reflective delay controller 220 through the second port P2. The circulator 240 may output the delay optical signal DS2 to the light emitting unit 230 through the third port P3.

In an embodiment, the circulator 240 may provide a first path from the mode locking laser 210 to the reflective delay controller 220. However, the scope of the present disclosure is not limited thereto, and the first path provided by the circulator 240 may further include other components. This will be described with reference to FIG. 6.

In an embodiment, the circulator 240 may provide a second path from the reflective delay controller 220 to the light emitting unit 230. However, the scope of the present disclosure is not limited thereto, and the second path provided by the circulator 240 may further include other components. This will be described with reference to FIG. 6.

Figure 5:
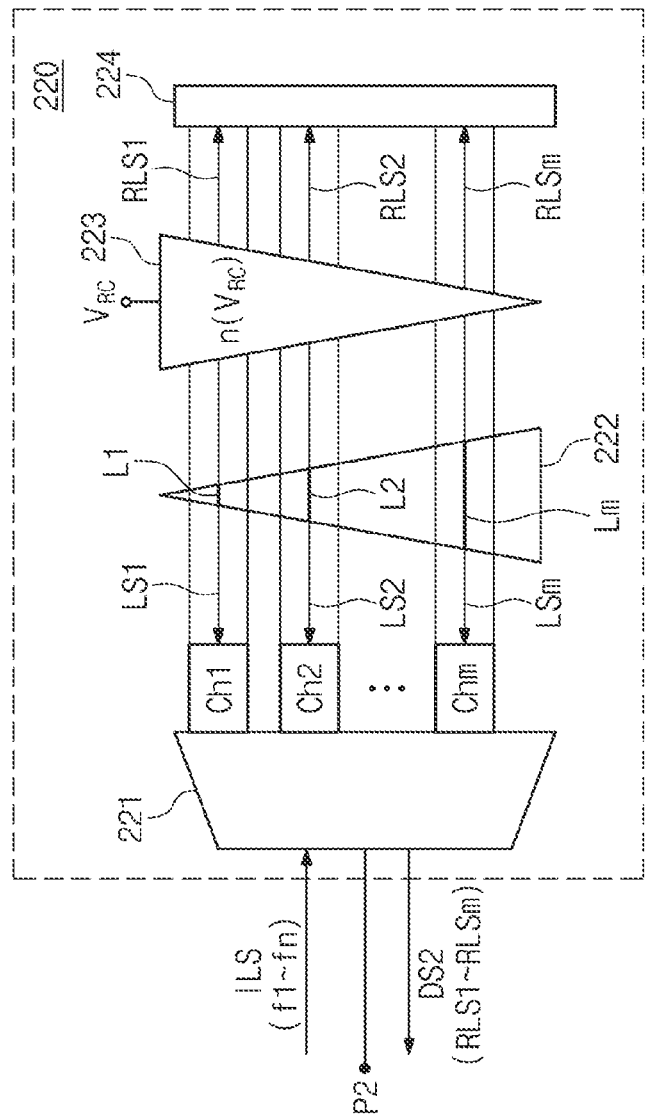
FIG. 5 is a detailed diagram of a reflective delay controller of FIG. 4.

FIG. 5 is a detailed diagram of the reflective delay controller 220 of FIG. 4. Referring to FIG. 5, the reflective delay controller 220 may include a channel separator 221, a path delay unit 222, a refractive index controller 223, and a reflector 224.

The channel separator 221 may receive the input optical signal ILS from the second port P2. The channel separator 221 may separate the input optical signal ILS based on the frequency components f1 to fn of the input optical signal ILS and may output the first to m-th sub-optical signals LS1 to LSm to the corresponding first to m-th channels Ch1 to Chm. The first to m-th channels Ch1 to Chm may be paths through which optical signals are transmitted. The first to m-th channels Ch1 to Chm may be physically or spatially separated from each other.

Furthermore, the channel separator 221 may combine the first to m-th reflective sub-optical signals RLS1 to RLSm from the first to m-th channels Ch1 to Chm. The channel separator 221 may output the delay optical signal DS2 to the second port P2. The delay optical signal DS2 may be signals obtained by combining first to m-th reflective sub-optical signals RLS1 to RLSm thus sequentially delayed.

That is, the channel separator 221 may perform functions similar to those of the demultiplexer 121 and the multiplexer 124 of FIG. 2.

Like the path delay unit 122 of FIG. 2, the path delay unit 222 may adjust the lengths L1 to Lm of optical paths of the first to m-th channels Ch1 to Chm. Like the refractive index controller 123 of FIG. 2, the refractive index controller 223 may adjust the refractive index ($n(V_{RC})$) of each of the first to m-th channels Ch1 to Chm. That is, the path delay unit 222 and the refractive index controller 223 may perform similar functions to those of the path delay unit 122 and the refractive index controller 123 of FIG. 2.

The reflector 224 may receive the first to m-th sub-optical signals LS1 to LSm from the first to m-th channels Ch1 to Chm. The reflector 224 may reflect the first to m-th sub-optical signals LS1 to LSm. The reflector 224 may output the first to m-th reflective sub-optical signals RLS1 to RLSm to the first to m-th channels Ch1 to Chm. The first to m-th reflective sub-optical signals RLS1 to RLSm may be signals obtained by reflecting the first to m-th sub-optical signals LS1 to LSm by the reflector 224.

The reflector 224 may reflect the sub-optical signals LS1 to LSm, and thus the sub-optical signals LS1 to LSm may pass through the first to m-th channels Ch1 to Chm twice in the reflective delay controller 220. For example, all of the first to m-th sub-optical signals LS1 to LSm and all of the first to m-th reflective sub-optical signals RLS1 to RLSm may pass through the first to m-th channels Ch1 to Chm. As such, optical path lengths for the first to m-th reflective sub-optical signals RLS1 to RLSm are twice as long as optical path lengths for the first to m-th sub-optical signals LS1 to LSm in FIG. 2. Accordingly, the first to m-th reflective sub-optical signals RLS1 to RLSm may be delayed twice as much as the first to m-th sub-optical signals LS1 to LSm in FIG. 2.

In an embodiment, the reflective delay controller 220 may be miniaturized and driven with low power. In more detail, the reflective delay controller 220 may control signals so as to pass through the first to m-th channels Ch1 to Chm twice to the reflector 224. Accordingly, under the condition that optical path length differences are the same as each other, the reflective delay controller 220 may be miniaturized and driven with low power as compared with the transmission delay controller 120 of FIG. 2.

The delay optical signal DS2 output from the channel separator 221 may have a delay time. The delay time may indicate a maximum deviation of the reflective sub-optical signals RLS1 to RLSm within one period of the delay optical signal DS2. For example, the delay time may be a time interval between a point in time when the reflective sub-optical signal RLS1 corresponding to the slowest frequency component (e.g., f1) is output within an arbitrary period and a point in time when the reflective sub-optical signal RLSm corresponding to the fastest frequency component (e.g., fn) is output within an arbitrary period.

The delay time $\Delta T$ of the reflective delay controller 220 is described with reference to Equation 2 below.

$$\Delta T = \frac{2\Delta L}{\frac{c}{n(V_{RC})}} \qquad \text{[Equation 2]}$$

Equation 2 is an equation indicating the delay time $\Delta T$ of the reflective delay controller 220. $\Delta T$ denotes a delay time. $\Delta L$ denotes a difference between the length L1 of the optical path of the first channel Ch1 and the length Lm of the optical path of the m-th channel Chm. 'c' is the speed of light. $n(V_{RC})$ is a refractive index of each of the first to m-th channels Ch1 to Chm, and is the function of $V_{RC}$. $V_{RC}$ is an external voltage.

In an embodiment, when the refractive index ($n(V_{RC})$) of each of the first to m-th channels Ch1 to Chm is 1.5 and a difference $\Delta L$ between the length L1 of the first optical path and the length Lm of the m-th optical path is 50 mm, the delay time $\Delta T$ may be 5000 ps.

That is, similarly to Equation 1, Equation 2 may indicate that the delay time $\Delta T$ is proportional to a difference between the degree of refraction of the optical path L1 of the first channel and the degree of refraction of the optical path Lm of the m-th channel and the difference ΔL between the length L1 of the optical path of the first channel Ch1 and the length Lm of the optical path of the m-th channel Chm.

However, unlike the transmission delay controller 120 of FIG. 2, the reflector 224 may reflect the first to m-th sub-optical signals LS1 to LSm. Accordingly, the reflective delay controller 220 may allow signals so as to pass through the first to m-th channels Ch1 to Chm twice. Accordingly, the delay time ΔT in Equation 2 may be twice as great as the delay time ΔT in Equation 1.

For example, when the refractive index $(n(V_{RC}))$ of each of the first to m-th channels Ch1 to Chm is 1.5 and the difference ΔL between the length L1 of the first optical path and the length Lm of the m-th optical path is 50 mm, the delay time ΔT in the transmission delay controller 120 may be 250 ps and, on the other hand, the delay time ΔT in the reflective delay controller 220 may be 500 ps.

Figure 6:
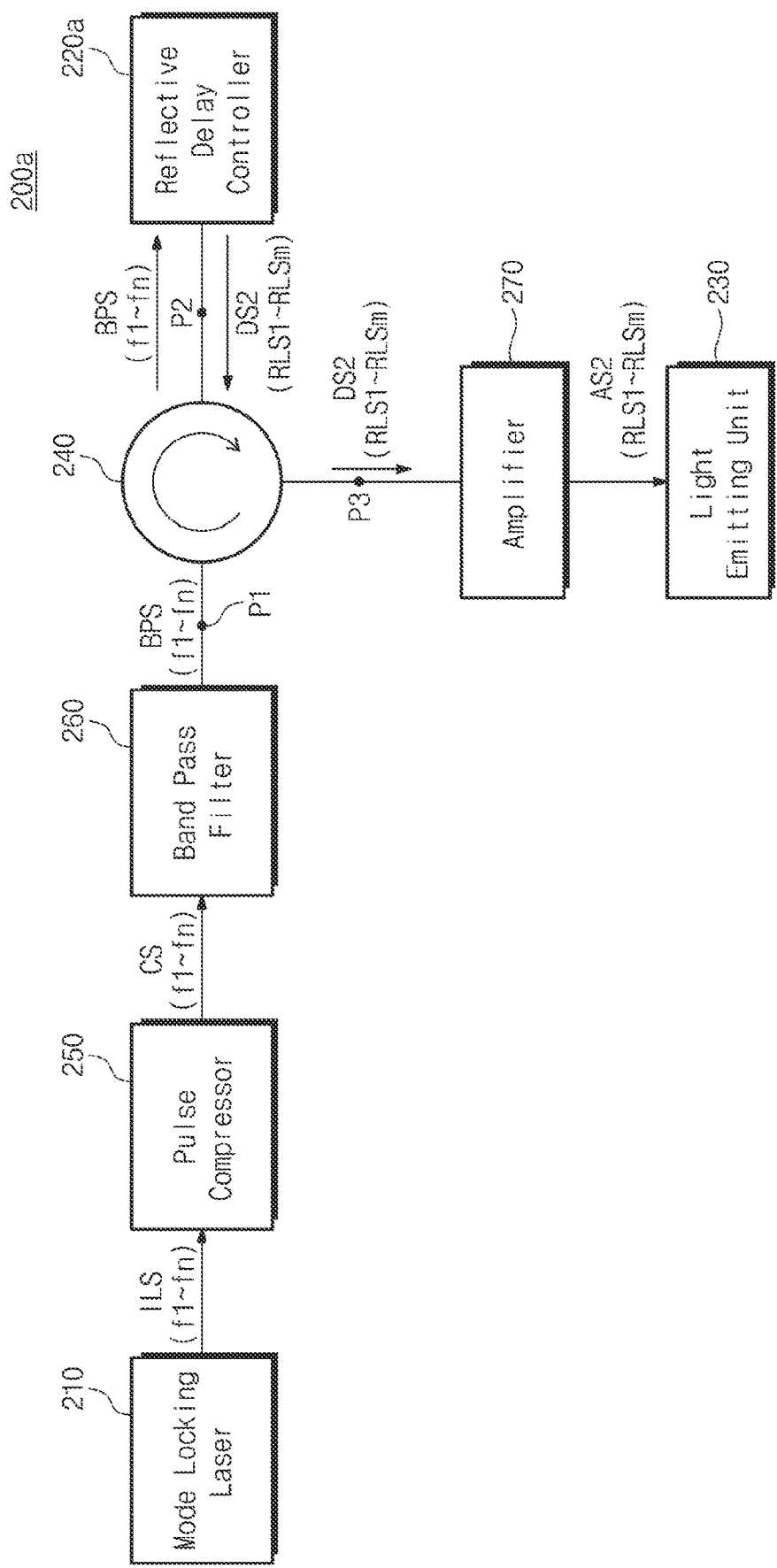
FIG. 6 is a detailed block diagram of the frequency swept source apparatus of FIG. 4.

FIG. 6 is a detailed block diagram of the frequency swept source apparatus of FIG. 4. Referring to FIG. 6, a frequency swept source apparatus 200a may include the mode locking laser 210, a reflective delay controller 220a, the light emitting unit 230, the circulator 240, a pulse compressor 250, a band pass filter 260, and an amplifier 270.

The mode locking laser 210 and the light emitting unit 230 are similar to the mode locking laser 210 and the light emitting unit 230 of FIG. 4, and thus, additional description will be omitted to avoid redundancy. The pulse compressor 250 and the band pass filter 260 are similar to the pulse compressor 140 and the band pass filter 150 of FIG. 3, and thus, additional description will be omitted to avoid redundancy.

The reflective delay controller 220a may receive the band pass signal BPS from the circulator 240 through the second port P2. The reflective delay controller 220a may generate the first to m-th reflective sub-optical signals RLS1 to RLSm having a plurality of frequency components f1 to fn based on the band pass signal BPS. The reflective delay controller 220a may output the delay optical signal DS2 to the second port P2. The delay optical signal DS2 may be signals obtained by combining first to m-th reflective sub-optical signals RLS1 to RLSm thus sequentially delayed.

That is, the reflective delay controller 220a may perform a function similar to that of the reflective delay controller 220. Unlike the reflective delay controller 220 of FIG. 4 that directly receives the input optical signal ILS, the reflective delay controller 220a may receive the band pass signal BPS.

The circulator 240 may receive the band pass signal BPS through the first port P1. The circulator 240 may output the band pass signal BPS to the reflective delay controller 220a through the second port P2. Moreover, the circulator 240 may receive the delay optical signal DS2 from the reflective delay controller 220a. The circulator 240 may output the delay optical signal DS2 to the amplifier 270 through the third port P3. That is, the circulator 240 may perform a function similar to that of the circulator 240 of FIG. 4.

In an embodiment, the circulator 240 may provide a first path. The first path may be a path through which a signal sequentially passes through the mode locking laser 210, the pulse compressor 250, the band pass filter 260, the circulator 240, and the reflective delay controller 220a.

In an embodiment, the circulator 240 may provide a second path. The second path may be a path through which a signal sequentially passes through the reflective delay controller 220a, the circulator 240, the amplifier 270, and the light emitting unit 230.

The amplifier 270 may receive the delay optical signal DS2 from the third port P3. The amplifier 270 may amplify the delay optical signal DS2. The amplifier 270 may output an amplified optical signal AS2 to the light emitting unit 230. In an embodiment, the amplifier 270 may be a GE that equally amplifies a gain of the received delay optical signal DS2. That is, the amplifier 270 may perform a function similar to that of the amplifier 160 of FIG. 3.

Figure 7A:
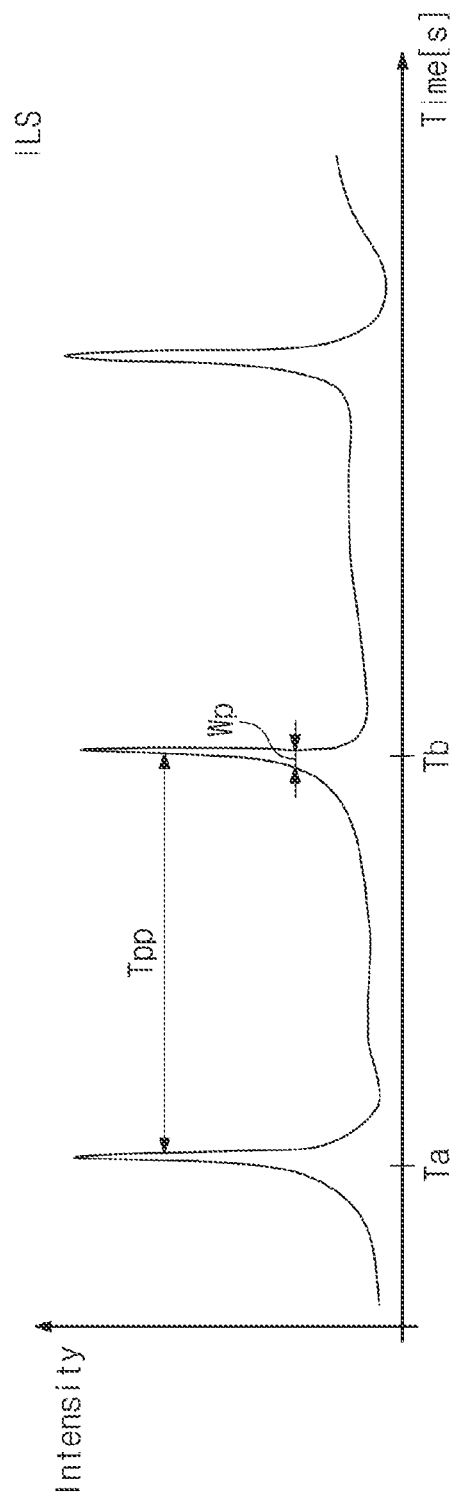
FIGS. 7A and 7B are graphs illustrating an input optical signal of a mode locking laser.
Figure 7B:
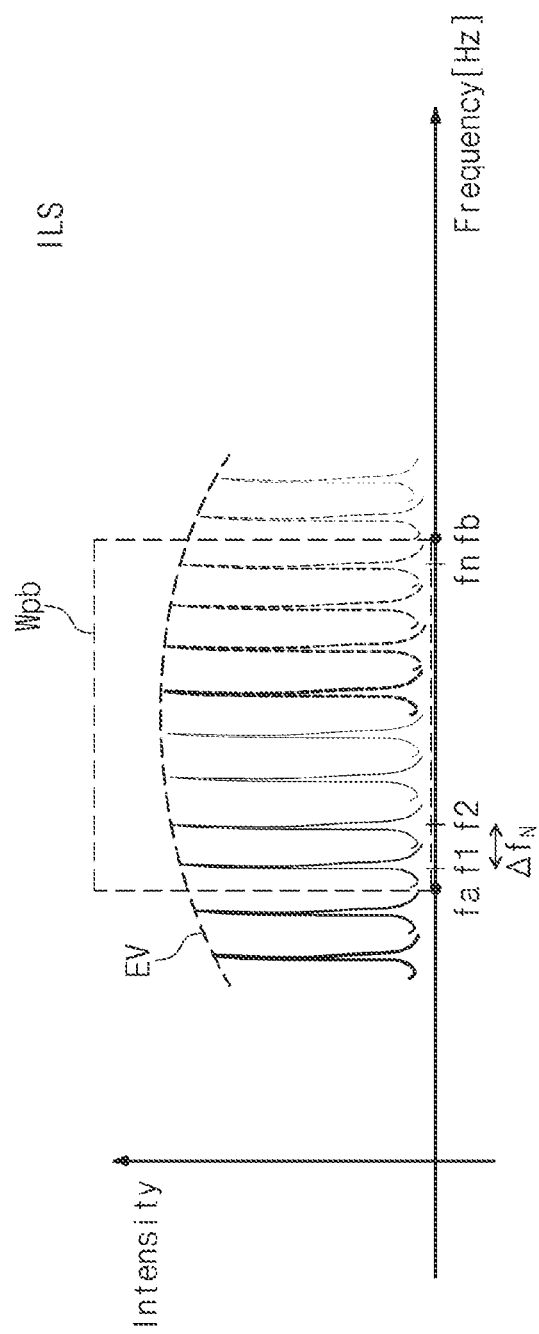

FIGS. 7A and 7B are graphs illustrating an input optical signal of a mode locking laser.

FIG. 7A is a graph illustrating the input optical signal ILS of a frequency swept source apparatus in a time domain. For example, a waveform shown in FIG. 7A may be the input optical signal ILS in FIGS. 1 to 6 described above. The horizontal axis may indicate a time. The vertical axis may indicate intensity.

Referring to FIG. 7A, the input optical signal ILS may have an input period Tpp. The input period Tpp may refer to a time interval between pulses in an input optical signal. For example, the input period Tpp may be a time interval between a first time point Ta, at which a first pulse is generated, and a second time point Tb, at which the second pulse is generated. A pulse included in the input optical signal ILS may have an input pulse width Wp.

FIG. 7B is a graph illustrating the input optical signal ILS shown in FIG. 7A in a frequency domain. The horizontal axis may indicate a frequency. The vertical axis may indicate intensity. Referring to FIG. 7B, the input optical signal ILS is shown in a frequency domain. When Fourier transformation is performed on the input optical signal ILS of FIG. 7A, optical combs having a frequency interval $(\Delta f_N(=1/Tpp))$ may be shown.

In the frequency domain, optical combs of the input optical signal ILS may form an envelope EV. In an embodiment, a frequency band of the envelope EV of the input optical signal ILS may be several terahertz (THz).

In an embodiment, when a pulse width of the input optical signal ILS in a time domain is compressed, a bandwidth of the envelope EV may be expanded. For example, the envelope EV of the compression optical signal CS output from the pulse compressor 140 of FIG. 3 may be wider than the envelope EV of the input optical signal ILS of FIG. 7B.

For example, when Fourier transformation is performed on the input optical signal ILS having a period of 1 ns, optical combs having a frequency interval $\Delta f_N$ of 1 GHz may appear. In more detail, for the envelope EV of 3 THz bandwidth, 3000 (3 THz/1 GHz) optical combs having a frequency interval $\Delta f_N$ of 10 GHz may be generated.

In an embodiment, the input optical signal ILS may include optical combs within a passband Wbp in the frequency domain. For example, the input optical signal ILS may include the first to n-th frequency components f1 to fn used for frequency swept. Other frequency components other than the first to n-th frequency components f1 to fn may be noise components unnecessary for frequency swept. The passband Wbp may be a frequency band between a first pass frequency fa and a second pass frequency fb, which is used to filter the first to n-th frequency components f1 to fn of the input optical signal ILS. For example, the band pass filter 150 of FIG. 3 may block frequency components other than frequency components in the passband Wbp.

Figure 8:
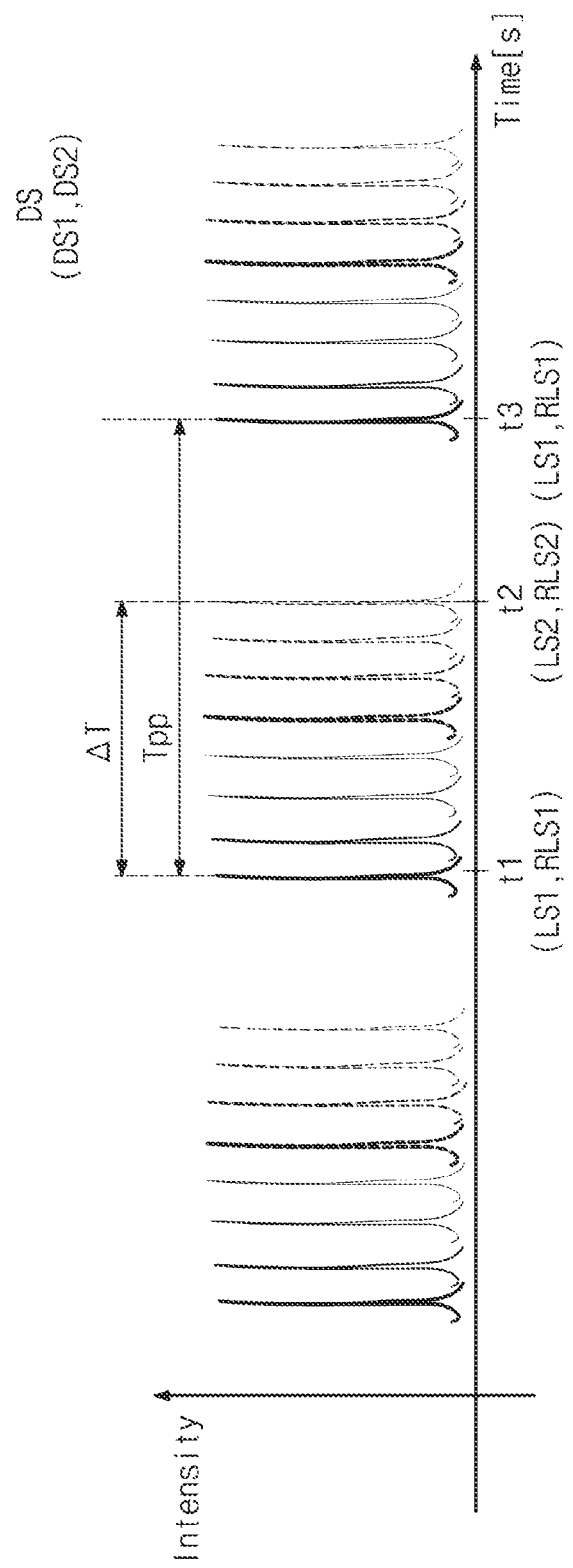
FIG. 8 is a graph illustrating a delay optical signal of a frequency swept source apparatus, according to an embodiment of the present disclosure.

FIG. 8 is a graph illustrating a delay optical signal of a frequency swept source apparatus, according to an embodiment of the present disclosure. Referring to FIG. 8, a delay optical signal DS in a frequency swept source apparatus is shown in a time domain. For example, the delay optical signal DS may be the delay optical signal DS1 of FIGS. 1 to 3 or the delay optical signal DS2 of FIGS. 4 to 6. The horizontal axis may indicate a time. The vertical axis may indicate intensity.

The delay optical signal DS may include the delayed first to m-th sub-optical signals LS1 to LSm or the delayed first to m-th reflective sub-optical signals RLS1 to RLSm. Each of the first to m-th sub-optical signals LS1 to LSm or each of the first to m-th reflective sub-optical signals RLS1 to RLSm may include at least one frequency component among the first to n-th frequency components of the input optical signal ILS. That is, unlike the input optical signal ILS of FIGS. 7A and 7B in which the first to n-th frequency components f1 to fn are output at the same or almost the same time point, the delay optical signal DS of FIG. 8 may be a signal obtained as the first to m-th sub-optical signals LS1 to LSm or the first to m-th reflective sub-optical signals RLS1 to RLSm, which correspond to the first to n-th frequency components f1 to fn, are sequentially delayed.

The delay time ΔT may indicate the maximum deviation of sub-optical signals within one period of the delay optical signal DS. For example, the delay time ΔT may be a time interval between a time point t1 at which the sub-optical signal LS1 corresponding to the slowest frequency component (e.g., f1) is output within an arbitrary period and a time point t2 at which the sub-optical signal LSm corresponding to the fastest frequency component (e.g., fn) is output within an arbitrary period. The delay time ΔT may be expressed with reference to Equation 1 or Equation 2 described above.

The input period Tpp may be a period of the delay optical signal DS. The input period Tpp of the delay optical signal DS may be the same as the input period Tpp of the input optical signal ILS. For example, the input period Tpp of the delay optical signal DS may be a time interval between the first time point t1, at which the first sub-optical signal LS1 is output, and a third time point t3 at which the next first sub-optical signal LS1 is output. The input period Tpp may be the same as the input period Tpp of FIG. 7.

Figure 9:
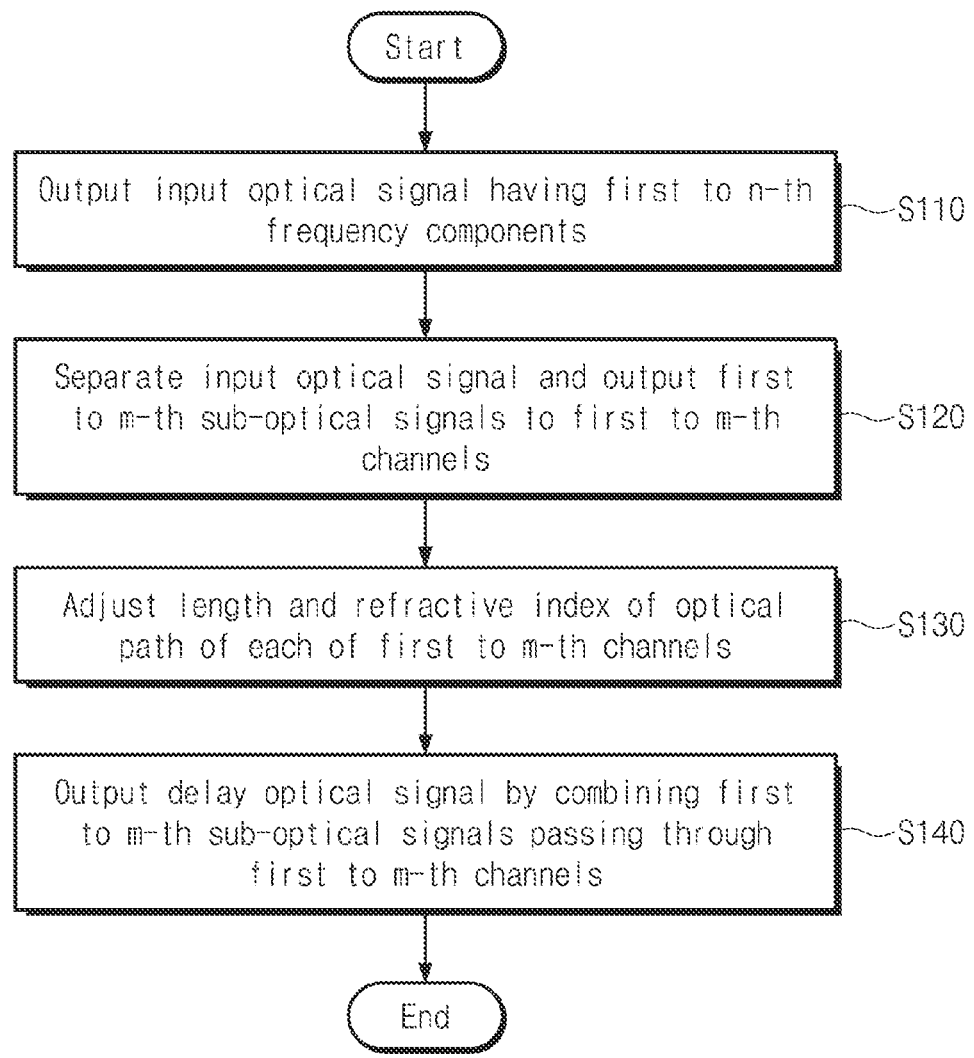
FIG. 9 is a flowchart illustrating a method of operating a frequency swept source apparatus, according to an embodiment of the present disclosure.

FIG. 9 is a flowchart illustrating a method of operating a frequency swept source apparatus, according to an embodiment of the present disclosure. Referring to FIG. 9, a method of operating a frequency swept source apparatus is illustrated. For example, the frequency swept source apparatus may be the frequency swept source apparatus 100 including the transmission delay controller 120 in FIG. 1 or the frequency swept source apparatus 100a including the transmission delay controller 120a in FIG. 3. In operation S110, the frequency swept source apparatus may output an input optical signal having first to n-th frequency components.

In operation S120, the frequency swept source apparatus may separate the input optical signal generated in operation S110 into first to m-th sub-optical signals. Each of first to m-th sub-optical signals may include at least one component among the first to n-th frequency components.

Afterward, the frequency swept source apparatus may output the first to m-th sub-optical signals to first to m-th channels. The first to m-th channels may be paths through which optical signals are transmitted. The first to m-th channels may be paths that are physically separated from one another.

In operation S130, the frequency swept source apparatus may adjust lengths of optical paths of the first to m-th channels differently from one another. Furthermore, the frequency swept source apparatus may adjust a refractive index of each of the first to m-th channels. In an embodiment, the frequency swept source apparatus may adjust the refractive index of each of the first to m-th channels so as to be increased in proportion to an external voltage.

In operation S140, the frequency swept source apparatus may output a delay optical signal by combining the first to m-th sub-optical signals passing through the first to m-th channels. In more detail, the frequency swept source apparatus may include a path delay unit and a refractive index controller. The first to m-th sub-optical signals may be signals that are sequentially delayed based on the lengths of the optical paths of the first to m-th channels adjusted by the path delay unit and the refractive index of each of the first to m-th channels adjusted by the refractive index controller.

Figure 10:
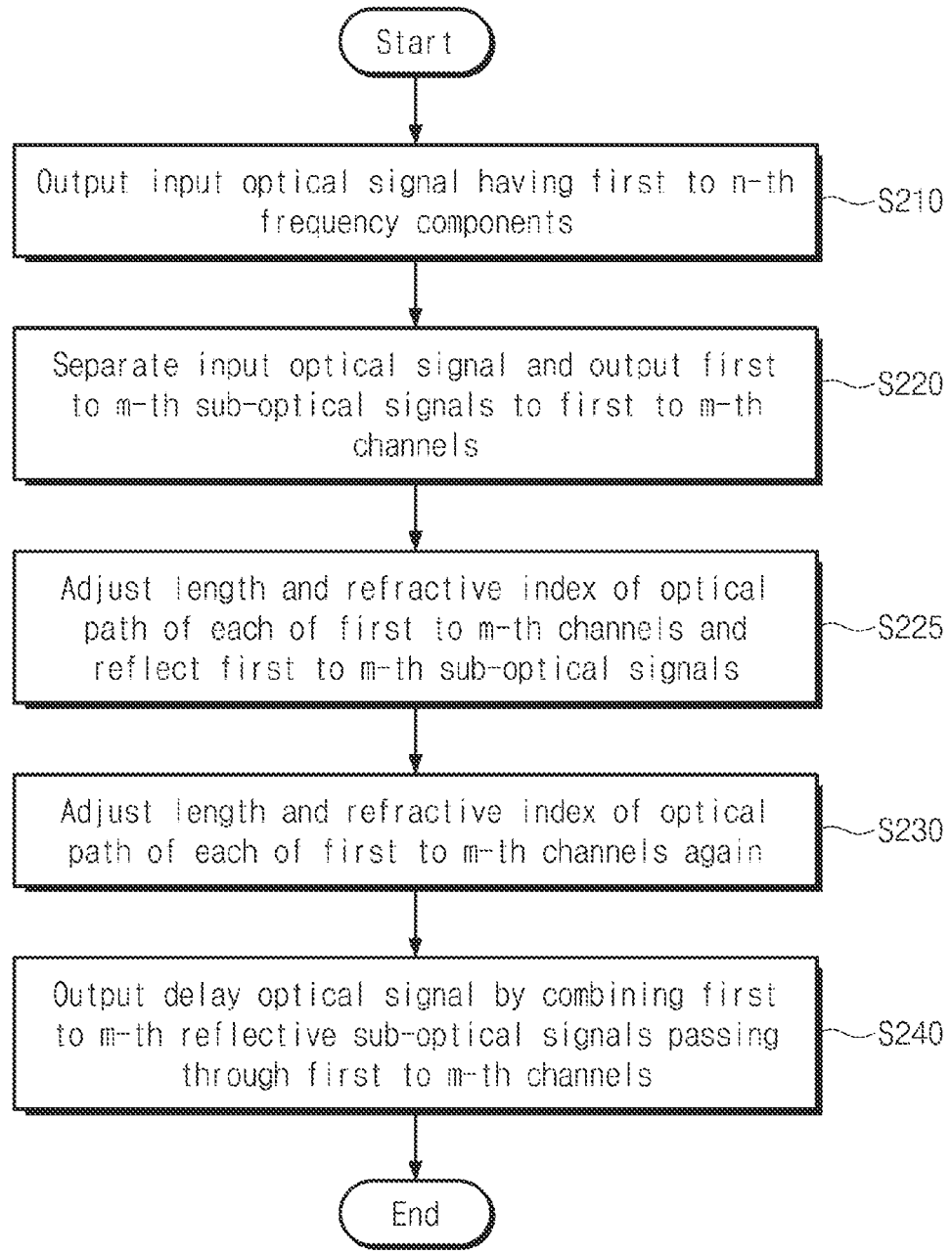
FIG. 10 is a flowchart illustrating a method of operating a frequency swept source apparatus, according to another embodiment of the present disclosure.

FIG. 10 is a flowchart illustrating a method of operating a frequency swept source apparatus, according to another embodiment of the present disclosure. Referring to FIG. 10, a method of operating a frequency swept source apparatus is illustrated. For example, the frequency swept source apparatus may be the frequency swept source apparatus 200 including the reflective delay controller 220 in FIG. 4 or the frequency swept source apparatus 200a including the reflective delay controller 220a in FIG. 6.

In operation S210, the frequency swept source apparatus may output an input optical signal having first to n-th frequency components.

In operation S220, the frequency swept source apparatus may separate the input optical signal generated in operation S210 into first to m-th sub-optical signals. Each of first to m-th sub-optical signals may include at least one component among the first to n-th frequency components. That is, operation S220 may perform an operation method similar to the operation method in operation S120 of FIG. 9.

In operation S225, the frequency swept source apparatus may adjust lengths of optical paths of the first to m-th channels differently from one another. Furthermore, the frequency swept source apparatus may adjust a refractive index of each of the first to m-th channels. The frequency swept source apparatus may adjust the refractive index of each of the first to m-th channels so as to be increased in proportion to an external voltage.

Afterward, in operation S225, the frequency swept source may output first to m-th reflective sub-optical signals to the first to m-th channels by reflecting first to m-th sub-optical signals.

In operation S230, the frequency swept source apparatus may adjust lengths of optical paths of the first to m-th channels differently from one another. The frequency swept source apparatus may adjust the refractive index of each of the first to m-th channels so as to be increased in proportion to an external voltage $V_{RC}$. That is, operation S225 may perform an operation method similar to the operation method in operation S220 described above. However, unlike operation S220, signals passing through the first to m-th channels may be the first to m-th reflective sub-optical signals. Signals may pass through the first to m-th channels twice through operation S230. Accordingly, under the condition that delays of optical signals according to channels are the same as one another, the frequency swept source apparatus may be miniaturized and driven with low power.

In operation S240, the frequency swept source apparatus may output a delay optical signal by combining the first to m-th reflective sub-optical signals passing through the first to m-th channels. In more detail, the frequency swept source apparatus may include a path delay unit and a refractive index controller. The first to m-th sub-optical signals may be signals that are sequentially delayed based on the lengths of the optical paths of the first to m-th channels adjusted by the path delay unit and the refractive index of each of the first to m-th channels adjusted by the refractive index controller.

The above description refers to detailed embodiments for carrying out the present disclosure. Embodiments in which a design is changed simply or which are easily changed may be included in the present disclosure as well as an embodiment described above. In addition, technologies that are easily changed and implemented by using the above embodiments may be included in the present disclosure. While the present disclosure has been described with reference to embodiments thereof, it will be apparent to those of ordinary skill in the art that various changes and modifications may be made thereto without departing from the spirit and scope of the present disclosure as set forth in the following claims.

According to an embodiment of the present disclosure, a frequency swept source apparatus for delaying an optical signal depending on a frequency component is provided.

Besides, a frequency swept source apparatus, which has stability, improved reliability, and an improved frequency swept repetition rate, is provided based on a transmission-type structure or the reflection-type structure for time delay.

While the present disclosure has been described with reference to embodiments thereof, it will be apparent to those of ordinary skill in the art that various changes and modifications may be made thereto without departing from the spirit and scope of the present disclosure as set forth in the following claims.

What is claimed is:

1. A frequency swept source apparatus, apparatus comprising:
    a mode locking laser configured to output an input optical signal having first to n-th frequency components;
    a transmission delay controller configured to generate first to m-th sub-optical signals, each of which includes at least one component of the first to n-th frequency components, based on the input optical signal and to output a delay optical signal obtained by sequentially delaying the first to m-th sub-optical signals,
    wherein the transmission delay controller includes:
    a demultiplexer configured to output the first to m-th sub-optical signals to first to m-th channels based on the input optical signal, respectively;
    a path delay unit configured to adjust lengths of optical paths of the first to m-th channels so as to be different from one another;
    a refractive index controller configured to adjust a refractive index of each of the first to m-th channels; and
    a multiplexer configured to combine the first to m-th sub-optical signals passing through the first to m-th channels and to output the delay optical signal,
    wherein the 'n' is a natural number, and
    wherein the 'm' is a natural number less than the 'n'.

2. The frequency swept source apparatus of claim 1, wherein the demultiplexer is further configured to:
    output the first sub-optical signal including a lowest frequency component among the first to n-th frequency components; and
    output the m-th sub-optical signal including a highest frequency component among the first to n-th frequency components.

3. The frequency swept source apparatus of claim 1, wherein the path delay unit is further configured to:
    adjust the lengths of the optical paths of the first to m-th channels so as to be increased sequentially.

4. The frequency swept source apparatus of claim 1, wherein the path delay unit is further configured to:
    adjust the lengths of the optical paths of the first to m-th channels so as to be decreased sequentially.

5. The frequency swept source apparatus of claim 1, wherein the refractive index controller is further configured to:
    increase the refractive index of each of the first to m-th channels in proportion to an external voltage.

6. The frequency swept source apparatus of claim 1, wherein the transmission delay controller is further configured to:
    determine a time interval between a first time point, at which the first sub-optical signal is output, and a second time point at which the m-th sub-optical signal is output, based on a length difference between the optical path of the first channel and the optical path of the m-th channel.

7. The frequency swept source apparatus of claim 1, wherein the transmission delay controller is further configured to:
    determine a time interval between a first time point, at which the first sub-optical signal is output, and a second time point at which the m-th sub-optical signal is output, based on the refractive index of each of the refractive index controller.

8. The frequency swept source apparatus of claim 1, wherein the 'n' is an integer multiple of the 'm'.

9. The frequency swept source apparatus of claim 1, further comprising:
    a pulse compressor configured to compress a pulse of the input optical signal from the mode locking laser and to output a compression optical signal;
    a band pass filter configured to block a noise component of the compression optical signal and to output a band pass signal to the transmission delay controller; and
    an amplifier configured to amplify the delay optical signal from the transmission delay controller.

10. A frequency swept source apparatus, apparatus comprising:
    a mode locking laser configured to output an input optical signal having first to n-th frequency components;
    a reflective delay controller configured to generate first to m-th sub-optical signals, each of which includes at least one component of the first to n-th frequency components, based on the input optical signal and to output a delay optical signal obtained by sequentially delaying the first to m-th sub-optical signals; and
    a circulator configured to provide a first path from the mode locking laser to the reflective delay controller and a second path from the reflective delay controller to a light emitting unit,
    wherein the reflective delay controller includes:
    a channel separator configured to output the first to m-th sub-optical signals to first to m-th channels based on the input optical signal, respectively, and to output the delay optical signal, which is obtained by combining first to m-th reflective sub-optical signals from the first to m-th channels, to the circulator;
    a path delay unit configured to adjust lengths of optical paths of the first to m-th channels so as to be different from one another;
    a refractive index controller configured to adjust a refractive index of each of the first to m-th channels; and
    a reflector configured to reflect the first to m-th sub-optical signals from the first to m-th channels and to output the first to m-th reflective sub-optical signals to the first to m-th channels,
    wherein the 'n' is a natural number, and
    wherein the 'm' is a natural number less than the 'n'.

11. The frequency swept source apparatus of claim 10, wherein the channel separator is further configured to:
- output the first sub-optical signal including a lowest frequency component among the first to n-th frequency components to the first channel based on the input optical signal; and
- output the m-th sub-optical signal including a highest frequency component among the first to n-th frequency components to the m-th channel based on the input optical signal.

12. The frequency swept source apparatus of claim 10, wherein the path delay unit is further configured to:
- adjust the lengths of the optical paths of the first to m-th channels so as to be increased sequentially.

13. The frequency swept source apparatus of claim 10, wherein the path delay unit is further configured to:
- adjust the lengths of the optical paths of the first to m-th channels so as to be decreased sequentially.

14. The frequency swept source apparatus of claim 10, further comprising:
- a pulse compressor configured to receive the input optical signal from the mode locking laser through the first path, to compress a pulse of the input optical signal, and to output a compression optical signal;
- a band pass filter configured to block a noise component of the compression optical signal and to output a band pass signal to the circulator through the first path; and
- an amplifier configured to receive the delay optical signal from the circulator through the second path, to amplify the delay optical signal, and to output an amplification optical signal to the light emitting unit through the second path.

* * * * *